United States Patent
Bedeschi et al.

(10) Patent No.: US 6,403,603 B1
(45) Date of Patent: Jun. 11, 2002

(54) PROCESS FOR THE PREPARATION OF 9-AMINO CAMPTOTHECIN

(75) Inventors: Angelo Bedeschi; Walter Cabri, both of Milan; Ilaria Candiani, Varese; Franco Zarini, Milan, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 08/284,129

(22) Filed: Aug. 2, 1994

(30) Foreign Application Priority Data

Aug. 6, 1993 (GB) .............................. 93163525

(51) Int. Cl.⁷ ..................... C07D 491/22; A61K 31/47
(52) U.S. Cl. ......................................... 514/283; 546/48
(58) Field of Search .............................. 546/48; 514/283

(56) References Cited

U.S. PATENT DOCUMENTS

| 4,894,456 A | 1/1990 | Wall et al. | |
| 5,225,404 A | * 7/1993 | Giovanella et al. | 514/283 |

FOREIGN PATENT DOCUMENTS

| DE | 2 150 234 | 4/1973 |
| EP | 0 538 534 | 4/1993 |

OTHER PUBLICATIONS

Chemical and Pharmaceutical Bulletin, vol. 39, No. 12, Dec. 1991, pp. 3183–3188, S. Samada, et al., "Sythesis And Antitumor Activity Of 20(S)–Camptothecin Derivatives: A Ring Modified And 7, 10–Disubstituted Camptothecins".

Journal of Labelled Compounds and Radiopharmaeuticals, vol. 18, No. 3, 1981, pp. 319–330, Peter E. Ronman, et al., "The Preparation Of Tritum And Deuterium–Labelled Camptothecin".

* cited by examiner

*Primary Examiner*—Bruck Kifle
(74) *Attorney, Agent, or Firm*—Oblon, Spivak, McClelland, Maier & Neustandt, P.C.

(57) ABSTRACT

9-Amino-20(S)-camptothecin (I) is prepared by reducing 12-nitro-20(S)-camptothecin (II); converting the resulting 12-amino-20(S)-camptothecin (III) into a compound of formula (IV)

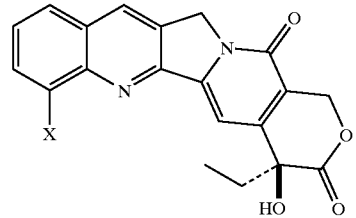

(IV)

wherein

X is a group which can be reductively removed; reacting the compound of formula (IV) with a nitrating agent, to obtain thereby the corresponding 9-nitro-20(S)-camptothecin compound of formula (V) substituted at the 12-position by the group X; reducing in a single step the compound of formula (V), so obtaining the 9-amino-20(S)-camptothecin of formula (I); or reducing the compound of formula (V), so obtaining the corresponding 9-amino-20(S)-camptothecin compound of formula (VI) substituted at the 12-position by the group X and reductively removing the X group from the compound of formula (VI), so obtaining 9-amino-20(S)-camptothecin.

15 Claims, No Drawings

PROCESS FOR THE PREPARATION OF 9-AMINO CAMPTOTHECIN

FIELD OF THE INVENTION

The present invention relates to a new process for the preparation of 9-amino-20 (S)-camptothecin of formula (I)

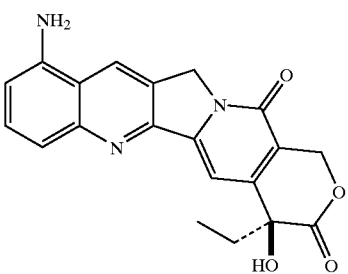

(I)

which is a known antitumor agent: Wani et al., J. Med. Chem. 1987, 30, 1774–1779; Hsiang et al., Cancer Res. 49, 4385–4389, Aug. 15, 1989; Cancer Res. 49, 1465–1469, Mar. 15, 1989.

BACKGROUND OF THE INVENTION

Totally synthetic approaches to 9-amino camptothecin have been widely described (U.S. Pat. No. 4,894,456 and U.S. Pat. No. 5,053,512). Total synthesis of the product, however, is neither desirable nor suitable for large scale production because it involves too many process steps that make the synthesis too long and, especially, too expensive.

A semisynthetic approach to 9-amino camptothecin is described, e.g., in JP-A-59-51289, published in 1984, starting from the known natural product camptothecin: Cancer Chemotherapy Reports, part I, vol. 54, No. 6, December 1970, 461–470; J. Med. Chem., 1980, 23, 554–560; Science, vol. 246, November 1989, 1046–1048. The said semisynthetic approach involves the nitration of the naturally occurring camptothecin, followed by reduction of the 9-nitro derivative. That nitration, however, initially produces a 70/30 mixture of the undesired 12-nitro camptothecin derivative (70%) and of the desired 9-nitro camptothecin derivative (30%). The 9-nitro derivative is therefore formed only in a minor amount.

After the separation of the two nitration products, the 12-nitro derivative, which is itself biologically inactive (see, for instance, Wani C., Nicholas A. W., Wall M. E., J. Med. Chem., 1986, 29, 2358), must then be discharged, giving rise to waste treatment problems. The considerable drawback concerning the removal of the undesired 12-nitro derivative byproduct is particularly relevant for large scale production since large amounts of unuseful 12-nitro derivative are collected and need to be eliminated.

Moreover, following this semisynthetic approach, large quantities of natural camptothecin, which is highly expensive, are needed to produce small quantities of the desired antitumor agent 9-amino camptothecin. The low overall productivity and yields of this approach make the production of substantial amounts of the desired compound difficult. There is therefore a need for a process permitting increased productivity and yields compared to the above outlined semisynthetic approach to 9-amino camptothecin.

We have developed a new process which fulfils this purpose and, at the same time, resolves the waste product problems deriving from the production of consistent amounts of the undesired 12-nitro derivative. According to the invention, this 12-nitro derivative is recycled into the process through conversion into 9-amino camptothecin by easy and mild reaction conditions ensuring high yields and clean reaction products.

SUMMARY OF THE INVENTION

Accordingly, the present invention provides a new process for preparing 9-amino camptothecin of formula (I) starting from 12-nitro camptothecin of formula (II), according to the steps illustrated in Scheme I below:

Scheme I

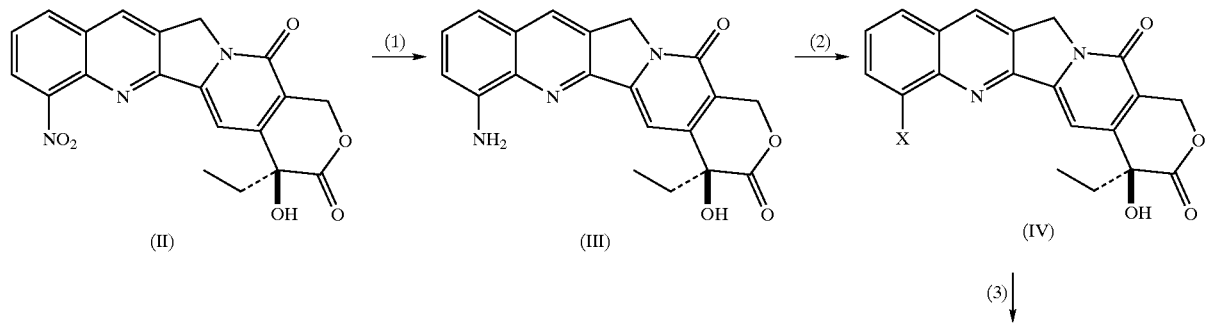

-continued

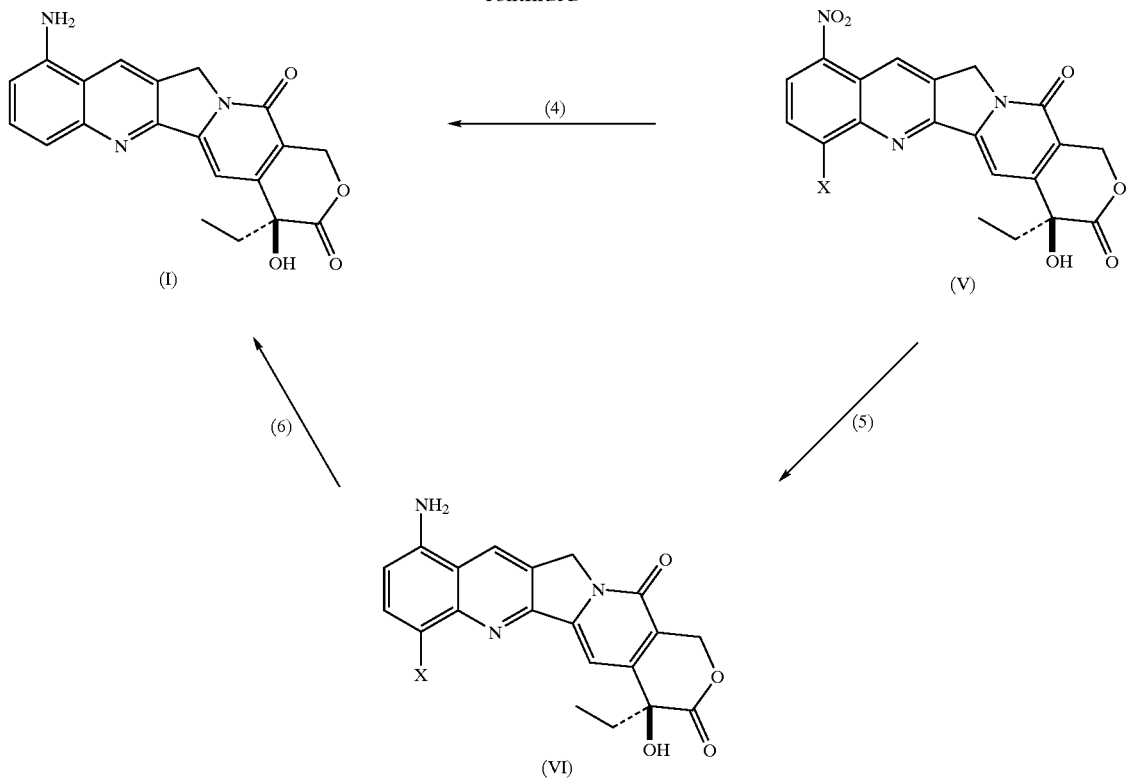

wherein X is a group which can be removed reductively.

The process includes the reductive transformation of the 12-nitro derivative of formula (II), into the 12-amino derivative of formula (III). This intermediate is in turn transformed into the corresponding diazo derivative, which is "in situ" transformed into a compound of formula (IV), wherein X is a group which can be reductively removed, e.g. a halogen.

Nitration of the 12-substituted derivative of formula (IV) affords with high selectivity and yields the corresponding 9-nitro-12-substituted derivative of formula (V). The subsequent reduction of the compound of formula (V) to give the 9-amino camptothecin compound of formula (I) may be performed either in a single step leading directly the compound of formula (I) or, alternatively, in two steps reducing first a compound of formula (V) to a compound of formula (VI) and, further, reducing a compound of formula (VI) to the compound of formula (I). The compound of formula (VI) may not be necessarily isolated.

In JP-A-59-51289 cited above and in published literature articles (see for instance Chem. Pharm. Bull. 1991, 39, 3183) much chemistry has been disclosed about the camptothecin molecule, including conversion of the 12-amino group into a corresponding 12-halo derivative, but it was used only for the purpose of synthesizing compounds for biological evaluation. The biological uselessness of the 12 substituted compounds (see, for instance Crow, R. T.; Crothers, D. M. J. Med. Chem. 1992, 35, 4160), and the chemical difficulties have then prevented any effort toward possible further modifications of the 12-substituted camptothecin derivatives.

In particular, the introduction of a nitro group on a 12-substituted derivative of this molecule is not known and looks problematic as it could give rise to mixtures of derivatives: different positions of the ring system, in fact, could undergo to reaction.

Furthermore, with reference to the removal of the X group from the compound (V) or (VI) it must be emphasized that, while the reductive removal of halogen atoms from quinolines is well known (see for instance Jones, G. The Chemistry of heterocyclic compounds, 32, I. p. 604–611) where, generally, the presence of bases is regarded as beneficial in order to achieve mild reaction conditions, on the contrary, in spite of the several years effort on the chemistry of camptothecin, nothing is known about group removal (e.g. removal of halogen groups) from camptothecin derivatives, and, more, camptothecin derivatives are known to be extremely base sensitive so that the recourse to a base would appear problematic.

Surprisingly we have now found that it Is possible to remove, e.g., a halogen atom from camptothecin in the presence of an organic or inorganic non-nucleophilic base. The present invention includes this aspect and is also based on the observation of the very weak basic and nucleophilic nature of the 9-amino group in camptothecin molecule. Indeed, the reduction of the 9-nitro group in 9-nitro-12-substituted derivatives of formula (V) would afford the 9-amino functionality and the so formed 9-amino group could then act as an in situ generated weak non-nucleophilic base, and, in principle, promote the reductive removal of group X, without decomposition.

On the other hand, the presence of the two substituents in the p-position to each other in a compound of formula (V) could be expected to have an undesired influence, and impede or render very difficult the double reduction step; low yields or decomposition of the desired product could be expected. In any case, the overall synthetic scheme illustrated above combining such a sequence of reactions, has never been reported, nor has its potential utility been recognized or exploited before.

DETAILED DESCRIPTION OF THE INVENTION

The present invention provides a process for preparing 9-amino camptothecin of formula (I)

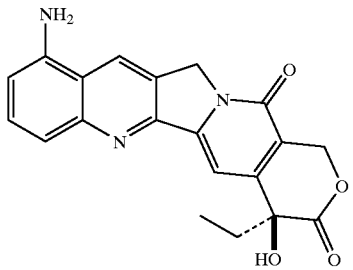

(I)

said process comprising:

(1) reducing the compound of formula (II)

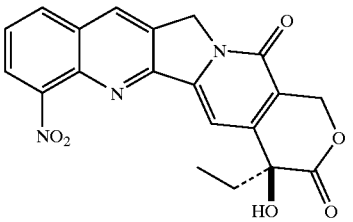

(II)

so obtaining the compound of formula (III)

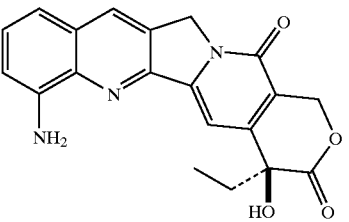

(III)

(2) converting the compound of formula (III) into a compound of formula (IV)

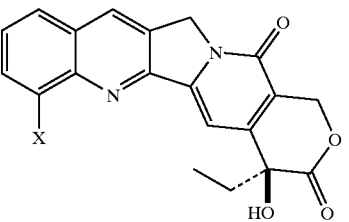

(IV)

wherein
X is a group which can be reductively removed;

(3) reacting a compound of formula (IV) with a nitrating agent so obtaining a compound of formula (V)

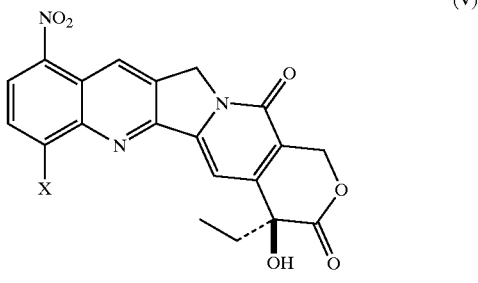

(V)

wherein X is as defined above, and (4) reducing in a single step a compound of formula (V) so obtaining the 9-amino camptothecin of formula (I) or, alternatively, (5) reducing a compound of formula (V) so obtaining a compound of formula (VI)

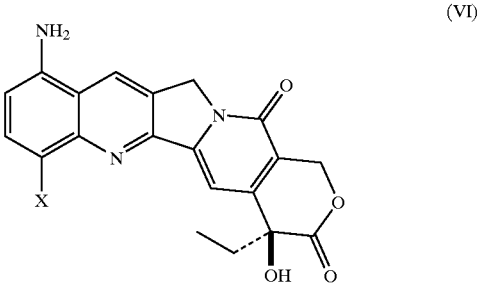

(VI)

wherein X is as defined above, and (6) reductively removing the X group from a compound of formula (VI) so obtaining the 9-amino camptothecin of formula (I).

Preferably the X group is a halogen, such as, e.g., Cl, I, Br or F, more preferably Cl or Br.

The reduction of the compound of formula (II) into the compound of formula (III) may be carried out, for example, with suitable reducing agents, or by catalytic reduction with suitable catalysts, in the presence of suitable reducing agents. For example, it may be performed as described in: J. March, Advanced Organic Chemistry, Third Edition, 1103. For instance, the reduction may be performed with reducing agents such as, e.g., $SnCl_2$, or other metals or metal salts, such as, e.g., Zn or Fe and their salts, in a suitable solvent such as, e.g., dilute or concentrate aqueous HCl, dilute aqueous protic acids, water, ethanol, methanol, or mixtures thereof, at a temperature of from about −20° C. to about 60° C., for a period which may vary from a few minutes to several days such as from about 5 minutes to about 3 days, for example from 4 hours to 24 hours; or by the use of catalytic amounts of metals which perform nitro group reduction, such as, e.g., palladium, platinum oxide, platinum, rhodium or ruthenium, in the presence of molecular hydrogen or hydrogen sources, such as, e.g., triethylammonium formate, formic acid, tributyltin hydride, cyclohexadiene, etc., in a suitable solvent, such as, e.g., dimethylformamide (DMF), MeOH, acetic acid, $CHCl_3$, dioxane, or mixtures thereof, at a temperature of from about 0° C. to about 100° C., for a time of from a few minutes, such as, e.g., 5 minutes, until $H_2$ consumption has ceased, e.g., about 3 days, and at a pressure of from about 1 atm to about 100 atm.

The conversion of the compound of formula (III) into a compound of formula (IV) may be carried out with a suitable reagent such as, for example, a copper(I) halide, through the formation of a diazoderivative which does not need to be isolated from the reaction mixture. The diazotisation reaction may be performed by the use of suitable diazotising agents, such as, e.g., $NaNO_2$ or organic nitrites in aqueous dilute protic acids, such as, e.g., HCl, HBr or $H_2SO_4$, or in organic solvents, at a temperature of from about $-20°$ C. to about $100°$ C., for a period which may vary from a few minutes to several hours, such as from about 5 minutes to about 24 hours. The resulting solution may then be reacted with from a stoichiometric amount to a large excess, for example up to a 10-fold molar excess, of a copper(I) halide, such as, e.g., CuCl or CuBr, or with iodide ions, optionally in the presence of an aqueous solution of the corresponding hydrogen halide acid that can be used as solvent, at a temperature of from about $0°$ C. to about $100°$ C., for a time which may vary from a few minutes to 1 day, such as from about 5 minutes to about 1 day.

The nitration of a compound of formula (IV) to obtain a compound of formula (V) may be performed with a nitrating agent, such as, e.g., nitric acid, mixtures of nitric and sulphuric acid, or other nitrating agents, such as, e.g., potassium nitrate or nitric acid and boron trifluoride, such as, boron trifluoride monohydrate (see for instance Olah, G. A., et al. Synthesis 1085, 1992), or nitric acid/trifluoromethansulfonic anhydride (ibid., 1087, 1992), at a temperature of from about $-20°$ C. to about $100°$ C., for a time which may vary from a few minutes to several days, such as from about 5 minutes to about 3 days, for example from about 4 hours to about 24 hours.

The single step reduction of a compound of formula (V) into the compound of formula (I) may be performed with suitable reducing agents, such as, e.g., molecular hydrogen or triethylammonium formate, formic acid, tributyltin hydride, cyclohexadiene, etc., in the presence of suitable catalysts either in homogeneous conditions, e.g., in the presence of palladium or platinum salts and of suitable phosphorus or nitrogen ligands, or heterogeneous conditions, e.g., in the presence of palladium, platinum oxide, platinum, rhodium or ruthenium as such, or supported on a suitable medium, such as, e.g., on carbon, on $CaCO_3$, on $BaSO_4$, on alumina, etc., in a suitable solvent such as, e.g., DMF, MeOH, acetic acid, $CHCl_3$, dioxane, or mixtures thereof, at a temperature of from about $0°$ C. to about $100°$ C., for a time which may vary from about 1 hour to about 3 days, and at a pressure of from about 1 atm to about 100 atm, optionally in the presence of an inorganic or organic base.

When alternatively the reduction of a compound of formula (V) into the compound of formula (I) is carried out in two separate steps, the first step may be performed with suitable reducing agents such as, e.g., those described above for the single step reduction of a compound of formula (V), for shorter times, e.g., for times of from a few minutes to several hours, such as from about 5 minutes to about 24 hours, if desired, isolatirg the intermediate derivative of formula (VI) and then performing the further reductive step of a compound of formula (VI) following the same reductive procedure described above for the reduction of a compound of formula (V) in a single step; or by means of reagents which give radical removal of halogens, such as, e.g., n-$Bu_3SnH$ in the presence of a radical initiator, such as, e.g., 2,2'-azobisisobutyronitrile (AIBN), or tristrimethylsilane, etc., in suitable solvents such as, e.g., benzene, toluene, $CHCl_3$, acetonitrile, DMF, or mixtures thereof, at a temperature which may vary from room temperature to solvent reflux temperature, for a time of a few minutes to several hours, such as, from about 5 minutes to about 24 hours.

Preferred reducing agents for the reduction from the compound of formula (II) to the compound of formula (III) are, e.g., $SnCl_2$, in dilute or concentrated aqueous HCl, at a temperature of from about $0°$ C. to about $60°$ C. for a period of from about 1 hour to about 2 days; or, by means of catalytic reduction, 5 or 10% Pd/C and molecular hydrogen in DMF, or $PtO_2$ and molecular hydrogen, at a temperature of from room temperature to about $60°$ C. for a time of from about 1 hour to about 24 hours, and with a hydrogen pressure of from about 1 atm to about 10 atm.

Preferred reagents for the conversion of the compound of formula (III) into a compound of formula (IV) are e.g., $NaNO_2$, amyl nitrite, tert-butyl nitrite, or organic nitrites, in aqueous or organic solvents such as, e.g., conc. HCl or HBr, dilute HCl or HBr, DMF, dioxane or $CH_2Cl_2$, at a temperature of from about $-20°$ C. to about $60°$ C., for a time of from about 10 minutes to about 12 hours. The resulting solution may then be reacted with from a stoichiometric amount to 10 equiv. of copper(I) halide, such as, e.g., CuCl or CuBr, or with iodide ions, optionally in the presence of aqueous solutions of the corresponding hydrogen halide acids that can be used as solvents, at a temperature of from room temperature to about $80°$ C., for a time which may vary from a few minutes to a few hours, such as from about 5 minutes to about 12 hours.

Preferred reagents for the conversion of a compound of formula (IV) into a compound of formula (V) are nitric acid, or mixtures of nitric and sulphuric acid, or potassium nitrate, or nitric acid and boron trifluoride monohydrate, or nitric acid/trifluoromethansulfonic anhydride, at a temperature of from about $-20°$ C. to about $60°$ C., for a time of from a few minutes to a several hours, such as, from about 5 minutes to about 24 hours.

Preferred reducing agents for the reduction in a single step of a compound of formula (V) into the compound of formula (I) are molecular hydrogen, triethylammonium formate, formic acid, or cyclohexadiene, in the presence of suitable catalysts, such as, e.g., palladium, platinum oxide, platinum and rhodium as such or supported on carbon, $CaCO_3$, $BaSO_4$, silica or alumina, in a suitable solvent, such as, e.g., DMF, MeOH, acetic acid, $CHCl_3$, dioxane, or mixtures thereof, optionally in the presence of a suitable organic base such as, e.g., pyridine or 2,6-alkyldisubstituted pyridines such as, e.g., 2,6-lutidine etc., or inorganic base such as, e.g., sodium or calcium carbonate etc., at a temperature of from about room temperature to about $80°$ C., for a time of from about 1 hour to about 2 days, and at a pressure of from about 1 atm to about 50 atm, and more preferably from about 1 to about 10 atm.

When alternatively, the reduction of a compound of formula (V) is performed in two separate steps, the preferred reagents for the first step are the same as those described above for the reduction of a compound of formula (V) in a single step, for shorter times, e.g., for times of from a few minutes, such as 5 minutes to about 6 hours, if desired, isolating the intermediate derivative of formula (VI), and then performing the second reductive step of a compound of formula (VI), following the same reductive procedure as described above for the reduction of a compound of formula (V) in a single step.

Preferred reagents for the radical removal of halogens, are n-$Bu_3SnH$, in the presence of radical initiators, such as AIBN, or tristrimethylsilane, etc., in suitable solvents such as benzene, toluene, $CHCl_3$, acetonitrile, DMF, or mixtures thereof, at a temperature of from room temperature to solvent reflux temperature, for a time of from few minutes to several hours, such as, from 5 minutes to 24 hours.

The mild reaction conditions, characterizing the process of the present invention, allow the (S) configuration at $C_{20}$ of the compound of formula (II) to be saved in the final compound 9-amino camptothecin of formula (I).

The starting compound of formula (II) is a known compound and may be prepared by known methods.

The present invention includes also in its scope a process for preparing 9-amino camptothecin of formula (I) by
(a) nitration of camptothecin of formula (VII)

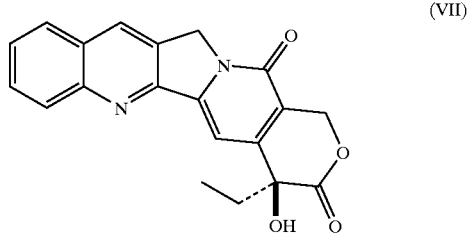

to give a mixture of 9-nitro-20(S)-camptothecin and 12-nitro-20(S)-camptothecin;
(b) separation of the 9-nitro-20(S)-camptothecin from the 12-nitro-20(S)-camptothecin;
(c) reduction of the separated 9-nitro-20(S)-camptothecin, to form thereby 9-amino-20(S)-camptothecin; and
(d) recycling the separated 12-nitro-20(S)-camptothecin through the said process steps (1) to (4) or process steps (1) to (3), (5) and (6) also to form thereby 9-amino camptothecin.

A further object of the present invention is a process for preparing camptothecin of the above formula (VII) comprising the reductive removal of the X group from compound of the above formula (IV).

The reductive removal of X the group from a compound of formula (IV) to obtain the camptothecin of formula (VII) may be carried out by using suitable reducing agents chosen from, e.g., molecular hydrogen or, for instance, triethylammonium formate, formic acid, cyclohexadiene, etc., in the presence of suitable catalysts, such as, e.g., palladium, platinum oxide, platinum, rhodium or ruthenium, as such or supported on a suitable medium, such as on carbon, on $CaCO_3$, on $BaSO_4$, on alumina, etc., in a suitable solvent such as DMF, MeOH, acetic acid, $CHCl_3$, dioxane, or mixtures thereof, in the presence of a suitable organic base, such as, for instance, pyridine or 2,6-alkyldisubstituted pyridines, such as, e.g., 2,6-lutidine, etc., at a temperature of from about 0° C. to about 100° C., for a time of from about 1 hour to about 3 days, and at a pressure of from about 1 atm to about 100 atm.

Preferred reducing agents, when in a compound of formula (IV) X is halogen, are molecular hydrogen, triethylammonium formate, formic acid, or cyclohexadiene, in the presence of suitable catalysts, such as, e.g., palladium, platinum oxide, platinum and rhodium as such, or supported on carbon, $CaCO_3$, $BaSO_4$, silica or alumina, in DMF, MeOH, acetic acid, $CHCl_3$, dioxane, or mixtures thereof, at a temperature of from about room temperature to about 80° C., for a time of from about 1 hour to about 24 hours, in the presence of an organic base, the preferred being pyridine, and 2,6-lutidine, and at a pressure of from 1 about atm to about 50 atm, and more preferably from about 1 to about 10 atm.

The 9-amino camptothecin of formula (I) and the camptothecin of formula (VII) are useful as inhibitors of topoi-somerase I. They are useful in the treatment of cancers, in particular leukaemia, colon and rectal tumours. The compounds may therefore be used to improve the condition of a patient suffering from such a cancer. They can be also used to alleviate such a cancer.

An effective amount of the 9-amino camptothecin or the camptothecin may thus be administered to a host in need thereof, typically a human. The active compound can be administered by an appropriate route, for example orally or parenterally such as, e.g., intravenously. A dose of from 0.1 to 60 mg of active compound can be given to a human patient per Kg body weight by these routes. A preferred dosage range is from 1 to 40 mg per Kg body weight.

The 9-amino camptothecin of formula (I) or the camptothecin of formula (VII) may be formulated for administrative purposes into a pharmaceutical composition with a pharmaceutically carrier or diluent. Any suitable carrier or diluent may be employed, depending upon the route of administration. Suitable types of formulations are described in U.S. Pat. No. 5106742 and WO91/05556.

The following Examples illustrate the preparation of the intermediates and compounds of the present invention and do not limit the scope of the invention.

EXAMPLE 1

12-Amino-20(S)-camptothecin

To a stirred solution/suspension of 12-nitro-20(S)-camptothecin (20 g) in conc. HCl (300 ml), anhydrous $SnCl_2$ (41.9 g) was added at 0–5° C., and the resulting mixture was stirred continuously at room temperature overnight. The solid is filtered and washed with small amounts of conc. HCl. The yellow solid was then suspended in water, and the pH adjusted to about 2 with solid sodium bicarbonate added in portions. The solid was collected by filtration, washed with water till neutral, then with ethanol and diethyl ether. After drying 10.5 g of the title compound were obtained.

$^1$NMR (DMSO-$d_6$), δ ppm: 0.88 (3H, t, J=7.2 Hz); 1.83 (2H, m); 5.22 (2H, s); 5.40 (2H, s); 6.19 (2H, bs); 6.50 (1H, s) 6.9–7.4 (3H, m); 8.44 (1H, s).

EXAMPLE 2

12-Amino-20(S)-camptothecin.

A solution of 12-nitro-20(S)-camptothecin (1 g) in DMF (100 ml) was hydrogenated at atmospheric pressure and room temperature in the presence of 10% Pd/C (0.25 g) until $H_2$ consumption ceased. The resulting suspension was diluted with an equal amount of DMF and filtered. The solution was conceitrated in vacuo to small volume and the precipitated yellow solid was collected by filtration, washed with ethanol and ether. The title product was obtained as a yellow solid (0.8 g). It had the same physical properties of the compound of Example 1.

EXAMPLE 3

12-Chloro-20(S)-camptothecin.

Sodium nitrite (2.4 g) in 30 ml water, was added to 12-amino camptothecin (9 g) in 18% HCl (650 ml) at 0–5° C. with stirring. After 30 minutes the reaction mixture was dropped into a flask containing CuCl (12.2 g) and 18% HCl (250 ml) at a temperature of 70° C. Heating was continued for 1.5 hours. The reaction mixture was then poured into ice-water, and the aqueous mixture extracted with methylene chloride. The solvent was removed in vacuo and the solid taken up with ether, and filtered again to yield 5.5 g of the title product.

$^1$NMR (DMSO-d$_6$), δ ppm: 0.89 (3H, t, J=7.3 Hz); 1.86 (2H, m); 5.29 (2H, s); 5.42 (2H, s); 6.57 (1H, s); 7.36 (1H, s); 7.66 (1H, t, J=7.9 Hz) 8.0–8.1 (2H, m); 8.75 (1H, s).

EXAMPLE 4

12-Bromo-20(S)-camptothecin.

Sodium nitrite (2.4 g) in 30 ml water, was added to 12-amino-20(S)-camptothecin (9 g) in 16% HBr (650 ml) at 0–5° C. with stirring. After 30 minutes the reaction mixture was dropped into a flask containing CuBr (21.3 g) and 16% HBr (250 ml) at a temperature of 70° C. Heating was continued for 1.5 hours. The reaction mixture was poured in ice-water, and the aqueous mixture extracted with ethyl acetate. After evaporation of the solvent, the pure product was isolated by precipitation with ether. The title product was obtained as a yellow solid (6.1 g).

$^1$NMR (DMSO-d$_6$), δ ppm: 0.88 (3H, t, J=7.3 Hz); 1.86 (2H, m); 5.31 (2H, s); 5.43 (2H, s); 6.58 (1H, s); 7.37 (1H, s); 7.60 (1H, t, J=7.9 Hz); 8.1–8.2 (2H, m); 8.74 (1H, s).

EXAMPLE 5

9-Nitro-12-Chloro-20(S)-camptothecin.

12-chloro-20(S)-camptothecin (5 g) was dissolved/suspended in conc. H$_2$SO$_4$ (70 ml) and cooled to 0–5° C. with mechanical stirring. 70% HNO$_3$ (2.7 ml) was dropped into the reaction mixture over 20 minutes, and the reaction flask was then left to warm to room temperature. The stirring was continued overnight at room temperature. The reaction mixture was poured into ice-water, and the yellow solid was collected by filtration, washed with water, ethanol and ether. After drying there were obtained 4 g of the title product.

$^1$NMR (DMSO-d$_6$), δ ppm: 0.89 (3H, t, J=7.2 Hz); 1.86 (2H, m); 5.34 (2H, s); 5.44 (2H, s); 6.61 (1H, s); 7.39 (1H, s); 8.24 (1H, d, J=8.3 Hz); 8.48 (1H, d, J=8.3 Hz); 9.22 (1H, s).

EXAMPLE 6

9-Nitro-12-bromo-20(S)-camptothecin.

12-bromo-20(S)-camptothecin (5.5 g) was dissolved/suspended in conc. H$_2$SO$_4$ (80 ml) and cooled to 0–5° C. with mechanical stirring. 70% HNO$_3$ (3.1 ml) was dropped into the reaction mixture over 20 minutes, and the reaction flask was then left to warm to room temperature. The stirring was continued overnight at room temperature. The reaction mixture was poured into ice-water, and the yellow solid was collected by filtration, washed with water, ethanol and ether. After drying there were obtained 4.2 g of the title product.

$^1$NMR (DMSO-d$_6$), δ ppm: 0.88 (3H, t, J=7.3 Hz); 1.87 (2H, m); 5.35 (2H, s); 5.44 (2H, s); 6.61 (1H, s); 7.40 (1H, s);

8.39 (1H, d, J=8.4 Hz); 8.45 (1H, d, J=8.4 Hz); 9.20 (1H, s).

EXAMPLE 7

9-Amino-12-chloro-20(S)-camptothecin.

A solution of 9-nitro-12-chloro-20(S)-camptothecin (3 g) in DMF (50 ml) was hydrogenated at atmospheric pressure and temperature in presence of 10% Pd/C (0.1 g) for 2 hours. The reaction mixture was filtered, and the solution was concentrated in vacuo. The residue was chromatographed on a silica gel column to yield the title compound (2.5 g).

$^1$NMR (DMSO-d$_6$), δ ppm: 0.87 (3H, t, J=7.2 Hz); 1.86 (2H, m); 5.28 (2H, s); 5.42 (2H, s); 6.30 (2H, bs); 6.56 (1H, s); 6.75 (1H, d, J=8.4 Hz); 7.31 (1H, s); 7.66 (1H, d, J=8.4 Hz); 8.89 (1H, s).

EXAMPLE 8

9-Amino-20(S)-camptothecin.

A solution of 9-nitro-12-chloro-20(S)-camptothecin (3 g) in DMF (50 ml) was hydrogenated at atmospheric pressure and temperature in presence of 10% Pd/C (0.1 g) for 48 hours. The reaction mixture was filtered, and the solution was concentrated in vacuo. The residue was chromatographed on a silica gel column to yield the title. compound (1.5 g).

$^1$NMR (DMSO-d$_6$), δ ppm: 0.87 (3H, t, J=7.3 Hz); 1.85 (2H, m); 5.26 (2H, s); 5.41 (2H, s); 6.11 (2H, s); 6.50 (1H, s); 6.79 (1H, m ); 7.28 (1H, s); 7.3–7.5 (2H, m); 8.83 (1H, s).

EXAMPLE 9

9-Amino-20(S)-camptothecin.

A solution of 9-nitro-12-bromo-20(S)-camptothecin (3 g) in DMF (50 ml) was hydrogenated at atmospheric pressure and temperature in presence of 10% Pd/C (0.1 g) for 6 hours. The reaction mixture was filtered, and the solution was concentrated in vacuo. The residue was chromatographed on a silica gel column to yield the title compound (2.0 g). This compound had identical characteristic as the compound obtained in Example 8.

EXAMPLE 10

9-Amino-20(S)-camptothecin from 9-Amino-12-chloro-20(S) -camptothecin.

The reaction was performed as in Example 8 to yield the title product as a yellow solid, which was identical to the authentic product.

EXAMPLE 11

20(S)-Camptothecin from 12-Chloro-20(S)-camptothecin.

The reaction was performed as in Example 8, except that the reaction was performed in the presence of pyridine, and the reaction mixture was hydrogenated for 12 hours. The title product was isolated by column chromatography. It was identical to a sample of the authentic product.

EXAMPLE 12

20(S)-Camptothecin from 12-Bromo-20(S)-camptothecin.

The reaction was performed as in Example 11, except that the reaction was carried out for 6 hours, to yield the title product, which was identical to a sample of the authentic material.

What is claimed is:

1. A process for preparing a 9-amino camptothecin of formula (I)

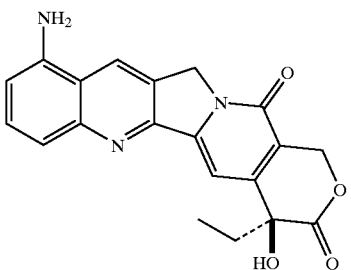

said process comprising the steps of:

(1) reducing the compound of formula (II)

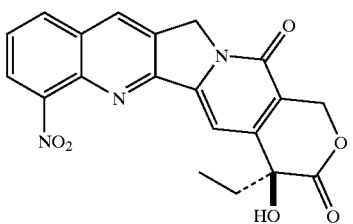

to form a compound of formula (III)

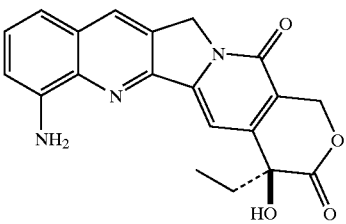

(2) converting the compound of formula (III) into a compound of formula (IV)

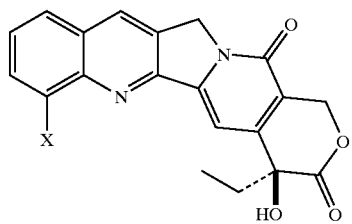

wherein
X is a halogen;

(3) nitrating the compound of formula (IV) to form a compound of formula (V)

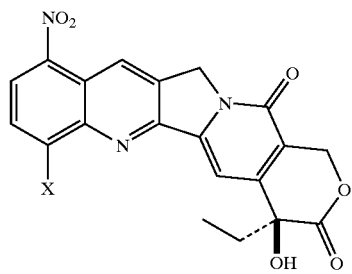

wherein X is as defined above; and (4) reducing in a single step the compound of formula (V), to form the 9-amino camptothecin of formula (I) or, alternatively, (5) reducing the compound of formula (V), to form a compound of formula (VI)

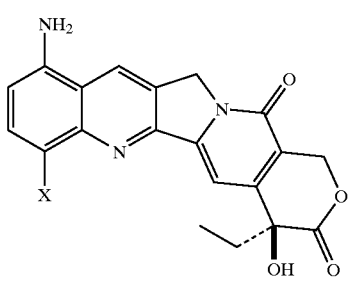

wherein X is as defined above, and (6) removing the X group by reducing the compound of formula (VI), to form the 9-amino camptothecin of formula (I).

2. A process according to claim 1, wherein step (1) is effected by using $SnCl_2$, Zn or Fe as a reducing agent or by catalytic, hydrogenation employing palladium, platinum oxide, platinum, rhodium or ruthenium.

3. A process according to any one of the preceding claims, wherein step (2) is effected by diazotisation of the compound of formula (III) and reaction of the diazotisation product with CuCl or CuBr.

4. A process according to any one of claims 1 and 2, wherein step (3) is effected by using a reagent selected from the group consisting of nitric acid; a mixture of nitric and sulfuric acids; potassium nitrate; nitric acid and boron trifluoride; and nitric acid and trifluoromethansulfonic anhydride.

5. A process according to any one of claims 1 and 2, wherein step (4), (5) or (6) is effected by using a reagent selected from the group consisting of molecular hydrogen, triethylammonium formate, formic acid, tributyltin hydride and cyclohexadiene.

6. The process according to the claim 1, further comprising the steps of:

(a) nitrating a camptothecin of formula (VII)

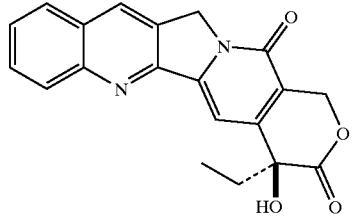
(VII)

to form a mixture of 9-nitro-20(S)-camptothecin and 12-nitro-20(S)-camptothecin;

(b) separating the 9-nitro-20(S)-camptothecin from the 12-nitro-20(S)-camptothecin;

(c) reducing the separated 9-nitro-20(S)-camptothecin, to form 9-amino-20(S)-camptothecin.

7. A process for the preparation of 9-amino camptothecin of formula (I)

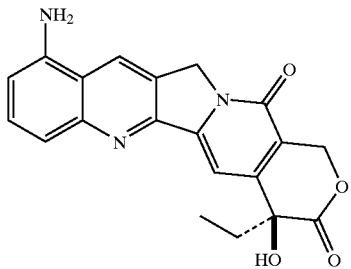
(I)

comprising the step of:

reducing a compound of formula (V)

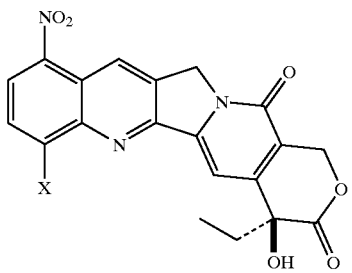
(V)

to form 9-amino camptothecin in a single step, wherein X is a halogen.

8. A process for the preparation of 9-amino camptothecin of formula (I)

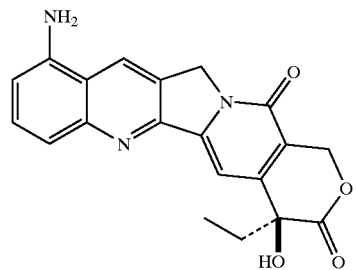
(I)

comprising the step of:

removing an X group by reducing a compound of formula (VI)

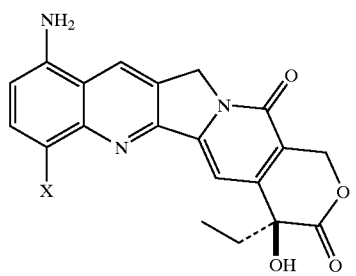
(VI)

to form 9-amino camptothecin of formula (I), wherein X is a halogen.

9. The process according to claim 7, further comprising the step of:

nitrating a compound of formula (IV)

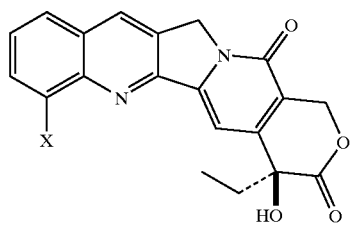
(IV)

to form the compound of formula (V).

10. A process for the preparation of a compound of formula (V)

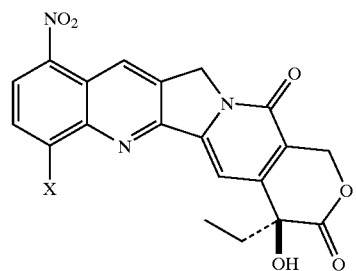
(V)

comprising the step of:

nitrating a compound of formula (IV)

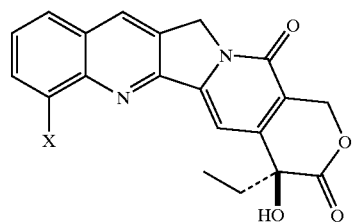

to form a compound of formula (V), wherein X is a halogen.

11. A process for the preparation of a compound of formula (VI)

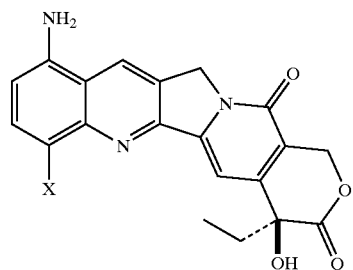

comprising the step of:

reducing a compound of formula (V)

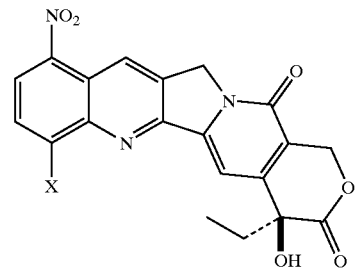

to form the compound of formula (VI).

12. The process of claim 1, wherein said process comprises steps (5) and (6).

13. The process of claim 1, wherein said process comprises step (4).

14. The process of claim 8, further comprising the step of:

reducing a compound of formula (V)

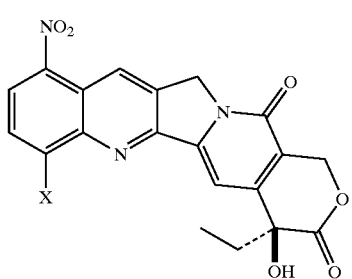

to form the compound of formula (VI).

15. The process of claim 9, further comprising the step of:

converting a compound of formula (III)

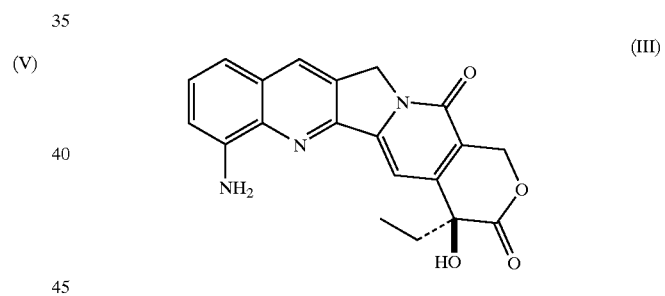

into the compound of formula (IV).

* * * * *